US009244104B2

(12) United States Patent
Hahl et al.

(10) Patent No.: US 9,244,104 B2
(45) Date of Patent: Jan. 26, 2016

(54) DETECTING A DIELECTRIC ARTICLE

(75) Inventors: Markus Hahl, Korntal-Muenchingen (DE); Oliver Grossmann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 474 days.

(21) Appl. No.: 13/808,699

(22) PCT Filed: May 11, 2011

(86) PCT No.: PCT/EP2011/057577
§ 371 (c)(1),
(2), (4) Date: Mar. 25, 2013

(87) PCT Pub. No.: WO2012/004028
PCT Pub. Date: Jan. 12, 2012

(65) Prior Publication Data
US 2013/0207674 A1    Aug. 15, 2013

(30) Foreign Application Priority Data

Jul. 7, 2010 (DE) .......................... 10 2010 031 034

(51) Int. Cl.
*G01R 27/26* (2006.01)
*G01F 23/26* (2006.01)
(Continued)

(52) U.S. Cl.
CPC .......... *G01R 27/2605* (2013.01); *G01F 23/266* (2013.01); *G01F 23/268* (2013.01); *G01N 27/221* (2013.01); *G01V 3/088* (2013.01)

(58) Field of Classification Search
CPC ............................ G01R 27/26; G01R 27/2605
USPC .................. 324/658–690, 548; 345/173, 174; 178/18.06, 19.03
See application file for complete search history.

(56) References Cited

U.S. PATENT DOCUMENTS 5,138,880 A   8/1992  Lee et al.
6,433,560 B1  8/2002  Hansen et al.
(Continued)

FOREIGN PATENT DOCUMENTS

DE   39 26 218 A1   1/1991
DE   199 16 979 A1  11/2000
EP   2 071 301 A1   6/2009

OTHER PUBLICATIONS

International Search Report corresponding to PCT Application No. PCT/EP2011/057577, mailed Jul. 20, 2011 (German and English language document) (8 pages).

*Primary Examiner* — Patrick Assouad
*Assistant Examiner* — Lamarr Brown
(74) *Attorney, Agent, or Firm* — Maginot, Moore & Beck LLP

(57) ABSTRACT

A device for detecting a dielectric object includes a first electrode and a second electrode. A first unit is configured to determine a first capacitance that exists between the first electrode and a common reference point and that is influenced by the object. A second unit is configured to determine a second capacitance that exists between the second electrode and the reference point and that is influenced by the object. The device further includes a control unit for actuating the first and second units and an evaluating unit that is configured to detect the object when the determined capacitances differ by more than a predetermined amount. The control unit is configured to actuate the units in such a manner that the capacitance determinations are carried out in succession. A switching unit is provided so as to electrically connect the electrode of the respective non-actuated unit to the common reference point.

7 Claims, 3 Drawing Sheets

(51) Int. Cl.
*G01N 27/22* (2006.01)
*G01V 3/08* (2006.01)

(56) References Cited

U.S. PATENT DOCUMENTS

| | | | |
|---|---|---|---|
| 6,791,342 B2* | 9/2004 | Ono | 324/658 |
| 6,867,601 B2* | 3/2005 | Morimoto | 324/661 |
| 6,894,507 B2* | 5/2005 | Morimoto | 324/661 |
| 7,138,809 B2* | 11/2006 | Nakamura et al. | 324/681 |
| 8,823,399 B1* | 9/2014 | Bharathan | 324/684 |
| 2004/0000918 A1 | 1/2004 | Sanoner et al. | |
| 2004/0217765 A1* | 11/2004 | Kitaoka | 324/683 |
| 2007/0205775 A1* | 9/2007 | Voelkel et al. | 324/662 |
| 2009/0045822 A1* | 2/2009 | Nosovitsky et al. | 324/686 |
| 2009/0107737 A1* | 4/2009 | Reynolds et al. | 178/18.06 |

* cited by examiner

DETECTING A DIELECTRIC ARTICLE

This application is a 35 U.S.C. §371 National Stage Application of PCT/EP2011/057577, filed on May 11, 2011, which claims the benefit of priority to Serial No. DE 10 2010 031 034.4, filed on Jul. 7, 2010 in Germany, the disclosures of which are incorporated herein by reference in their entirety.

BACKGROUND

For the capacitive location of a dielectric object, an electric field can be generated and it can then be determined whether the electric field is influenced by the object. In a variant, two electric fields are generated by means of two adjacent electrodes and a comparison of the capacitances at the two electrodes is carried out. If the capacitances differ by more than a predefined amount, then the presence of the object in the range of the electric fields can be inferred. This procedure can be used for any kind of object which has dielectric properties, for example a wooden beam in a lightweight wall.

The arrangement of adjacent electrodes is sensitive to all kinds of electrical conductors in their environment. The electrode arrangement is therefore set up at a certain spatial distance from an electric circuit which carries out the determination of the capacitance. For example, the electrode arrangement can be arranged on the same printed circuit board as the switching circuit, wherein there is a horizontal distance of a few centimeters between the electrodes and the switching circuit. As an alternative to this, the electrode arrangement can be mounted on a separate board so that there is a certain distance between the switching circuit and the electrodes in the vertical direction.

It is the object of the disclosure to specify a device and a method for detecting a dielectric object which allow better use of space.

SUMMARY

The disclosure achieves this object by a device and by a method with the characteristics of the disclosure. Dependent claims describe preferred embodiments.

A device according to the disclosure for detecting a dielectric object comprises a first and a second electrode, a first device for determining a first capacitance which exists between the first electrode and a common reference point and which can be influenced by the object, and a second device for determining a second capacitance which exists between the second electrode and the ground point and which can be influenced by the object. Furthermore, a control unit for actuating the devices and an evaluation unit for detecting the object are provided in the event that the determined capacitances differ from one another by more than a predefined amount. At the same time, the control unit is set up to actuate the device in such a way that the determinations are carried out successively, and a switching device is provided to electrically connect the electrode of the device which is not actuated at any one time to the common reference point. Advantageously, this enables parasitic capacitances between the first and the second electrode to be connected so that they do not influence the difference between the determinations.

The disclosure enables the influence of parasitic capacitances to be minimized when differentially determining the capacitance. The procedure according to the disclosure of sequential measurement while at the same time short-circuiting parasitic capacitances can be extended to any number of electrodes or electrode pairs.

Preferably, a third electrode is arranged in the region of the first and the second electrode. The third electrode can be used to achieve a shielding with respect to conductor tracks or electronic components in the region of the first two electrodes. Coupling capacitances resulting between the third and the first two electrodes are connected in the same way as the parasitic capacitances described above so that they do not influence the determination of the capacitance. This enables a measuring circuit to be designed in a compact manner; in particular, a distance between an evaluation circuit and the electrodes can be reducible to less than ten millimeters, preferably approx. 1.6 millimeters, which corresponds to the thickness of a normal printed circuit board, without detracting from the accuracy.

The third electrode can be arranged on a side of the first and the second electrode which faces away from the dielectric object. This enables a space-saving construction of the electrodes and of the assemblies for evaluating the electrode signals which are connected to the electrodes to be achieved. It is not necessary to distribute the assemblies and electrodes over a plurality of circuit boards or to maintain a large distance between the electrodes and the assemblies.

The devices for determining the capacitances can be set up to output time signals, the lengths of which in each case depend on the determined capacitances, and the evaluation unit can be set up to provide a time signal, the length of which depends on the difference between the capacitances. The time signals can be determined based on a charging or discharging of the capacitances. In this way, the capacitances can be determined with relatively low frequencies which can increase an accuracy of the determination. The time signal provided by the evaluation unit can be integrated and compared with a threshold value. An evaluation of this kind can be easily and reliably constructed in a known manner.

The control unit can be set up to periodically actuate the first and the second device for determining a capacitance with the same frequency, wherein a phase relationship between the periodic actuations can be varied in order to compensate for different capacitances in the absence of the object. In this way a simple and efficient synchronization of the procedures for determining the capacitances can be combined with an ability of the device to be easily calibrated.

A multiplicity of devices for determining capacitances between an electrode and the common reference point can be provided, wherein the control unit is set up to actuate only one of the devices at each point in time and the switching device is set up to electrically connect the electrodes of all devices which are not actuated to the common reference point.

A series of a multiplicity of capacitance determinations can therefore be carried out by means of spatially distributed electrodes.

A method according to the disclosure for detecting a dielectric object comprises steps of the determination of a first capacitance which exists between a first electrode and a ground point and which can be influenced by the object, the determination of a second capacitance which exists between a second electrode and the common reference point and which can be influenced by the object, and the detection of the object in the event that the determined capacitances differ from one another by more than a predefined amount. In doing so, the capacitances are determined successively and, during the determination by means of one of the electrodes, the respective other electrode is electrically connected to the common reference point.

Finally, a computer program product includes program code means for carrying out the method and can run on a processing device or be stored on a computer-readable data medium.

BRIEF DESCRIPTION OF THE DRAWINGS

The disclosure is now described in more detail with reference to the attached figures, in which.

DETAILED DESCRIPTION

Figure 1:
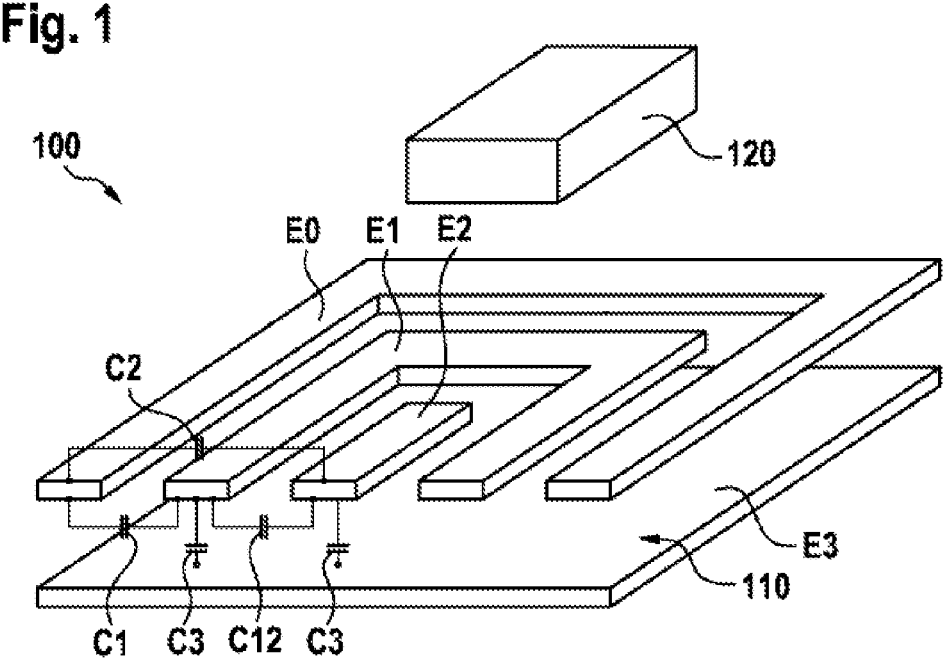
FIG. 1 shows an electrode arrangement.

FIG. 1 shows an electrode arrangement 100. With the electrode arrangement 100 shown in FIG. 1, a differential capacitance measurement is possible, thus enabling the object 120 to be found or determined. For example, the electrode arrangement 100 can be used as a beam finder for detecting a wooden beam hidden in a lightweight wall. Alternatively, the electrode arrangement 100 can also be used with a dielectric liquid in order to determine the level, wherein the electrode arrangement shown or a modified electrode arrangement can be used. Further applications which are based on a differential capacitance determination are likewise possible.

Electrodes E0-E3 are attached to both sides of a transparent printed circuit board (board) 110 shown.

The electrode E2, which is encompassed in a U-shape by the electrode E1, lies on the top side of the printed circuit board 110. In turn, the electrode E1 is encompassed in a U-shape by the electrode E0. The flat electrode E3 lies opposite the electrodes E0 to E2 on the bottom side of the printed circuit board 110. The electrodes E0 to E3 are in the form of copper surfaces which are stuck to the printed circuit board 110. The electrodes E0 to E3 can be formed on the printed circuit board 110 by an etching process, for example, with which further connecting elements for connecting electrical components can also be formed on the printed circuit board 110. A dielectric object 120 is situated above the printed circuit board 110 and the electrode E0.

While the electrodes E0 to E2 are connected to electrical components, the electrode E3 is either not further connected or can be connected with a high impedance to a circuit, for example by means of a controlled switch such as a transistor. The electrode E3 serves to shield the electrodes E0 to E2 from below. An influence of a measuring circuit attached here or of a measuring person on the electrodes E0 to E2 is minimized by the electrode E3. In some embodiments, the electrode E3 can also be omitted.

Capacitances C1, C2, C12 and C3, which in each case occur between the electrodes E0 to E3, are shown in the form of equivalent circuits. The capacitance C1 is formed between the electrodes E0 and E1, wherein the electrode E0 is connected to ground; correspondingly, the capacitance is formed between the electrodes E0 and E2. In other embodiments, the electrode E0 can be connected to any potential other than ground, as long as this potential can be used as an invariable reference point for determining the capacitances C1 and C2. The parasitic capacitance C12 occurs between the electrodes E1 and E2. A further parasitic capacitance C3 consists in a series circuit of partial capacitances between the electrodes E1 and E3 and E3 and E2 respectively.

In order to differentially detect the dielectric object 120, the capacitances C1 and C2 are normally charged or discharged simultaneously and a difference in time between the ends of the charging or discharging processes is measured. If this time difference exceeds a predefined time threshold, then the dielectric object 120 is inferred.

The parasitic capacitances C12 and C3 effect a coupling of the capacitances C1 and C2 to one another so that crosstalk occurs and the accuracy of the measurement, particularly for only small differences between the capacitances C1 and C2, is reduced. The parasitic capacitance C3 can also occur when, instead of the electrode E3, another conductive structure is arranged in the region of the electrodes E1 and E2, for example an electrical component or an operating element.

Figure 2:
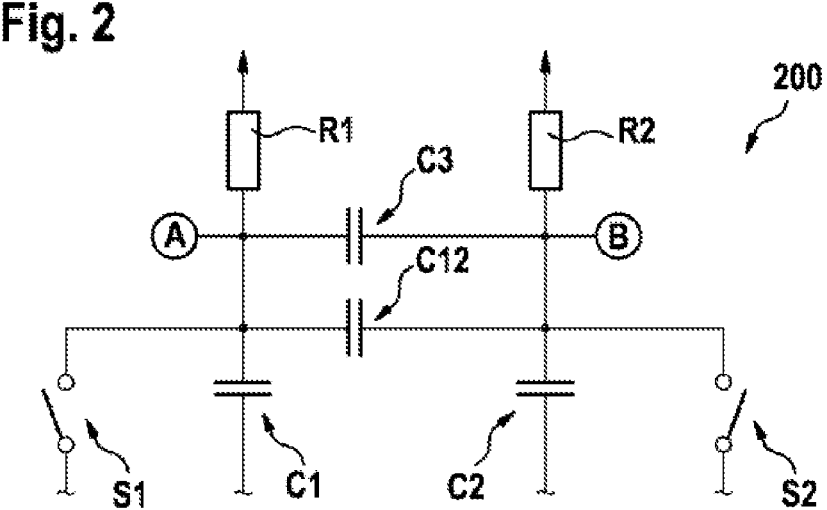
FIG. 2 shows a measuring circuit based on the electrode arrangement from FIG. 1.

FIG. 2 shows a measuring circuit 200 based on the electrode arrangement 100 from FIG. 1. The measuring circuit 200 shown is an equivalent circuit for explanation purposes; with an actual measuring circuit, the parasitic capacitances C12 and C3, for example, would be minimized. The electrode E0 is electrically connected to ground so that the bottom connection of the capacitances C1 and C2 in each case is connected to ground. The top connections of the capacitances C1 and C2 are connected to one another by means of the parasitic capacitances C12 and C3. The top connection of the capacitance C1 is referred to in the following as test point A. Test point A is connected to a constant operating voltage by means of a resistor R1, as symbolized by the arrow on the top connection of the resistor R1. In a corresponding manner, the top connection of the capacitance C2 is referred to in the following as test point B. Test point B is connected to the operating voltage by means of a resistor R2. A switch S1 is arranged parallel to the capacitance C2 and a switch S2 parallel to the capacitance C2.

The capacitance C1 is determined in that the capacitance C1 is charged via the resistor R1 and a time until the voltage at test point A has exceeded a predefined threshold value is determined. This threshold value is usually $\frac{2}{3}$ of the operating voltage when charging and $\frac{1}{3}$ of the operating voltage when discharging. The time determined is proportional to the capacitance C1. If a dielectric object 120 is located in the region of the electrodes E1 and E0, which form the capacitance C1, then the value of the capacitance C1 changes, which can be detected by a change in the time until the voltage at test point A rises above the threshold value. The capacitance C2 is determined in a similar manner in that the capacitance C2 is charged by means of the resistor R2 and the voltage at test point B is compared with a threshold value.

The parasitic capacitances C3 and C12 electrically couple the capacitances C1 and C2 so that, with the described procedure, an actual difference between the capacitances C1 and C2 is greater than a verifiable difference.

If the capacitances C1 and C2 are not determined simultaneously but successively, then the switch S2 can be closed while the capacitance C1 is determined, and the switch S1 can be closed while the capacitance C2 is determined. If the switch S2 is closed, then the capacitance C2 is short-circuited and the parasitic capacitances C12 and C3 lie parallel to the capacitance C1. The capacitance values are summed so that the capacitance C1+C12+C3 is determined. The switch S2 is then opened and the switch S1 closed, thus enabling the capacitance C2+C12+C3 to be determined. As C12 and C3 are independent of the effect of a dielectric object 120, they affect the two capacitance determinations to an equal extent. A comparison of the time which is required to charge the capacitance C1+C12+C3 to a predefined voltage with the time which is necessary for a corresponding charging of the capacitance C2+C12+C3 allows the constant portion resulting from the parasitic capacitances C12, C3 to be eliminated. The resulting time difference is therefore dependent on the capacitance C1 and C2, and the parasitic capacitances C12 and C3 do not affect the measurement.

Figure 3:
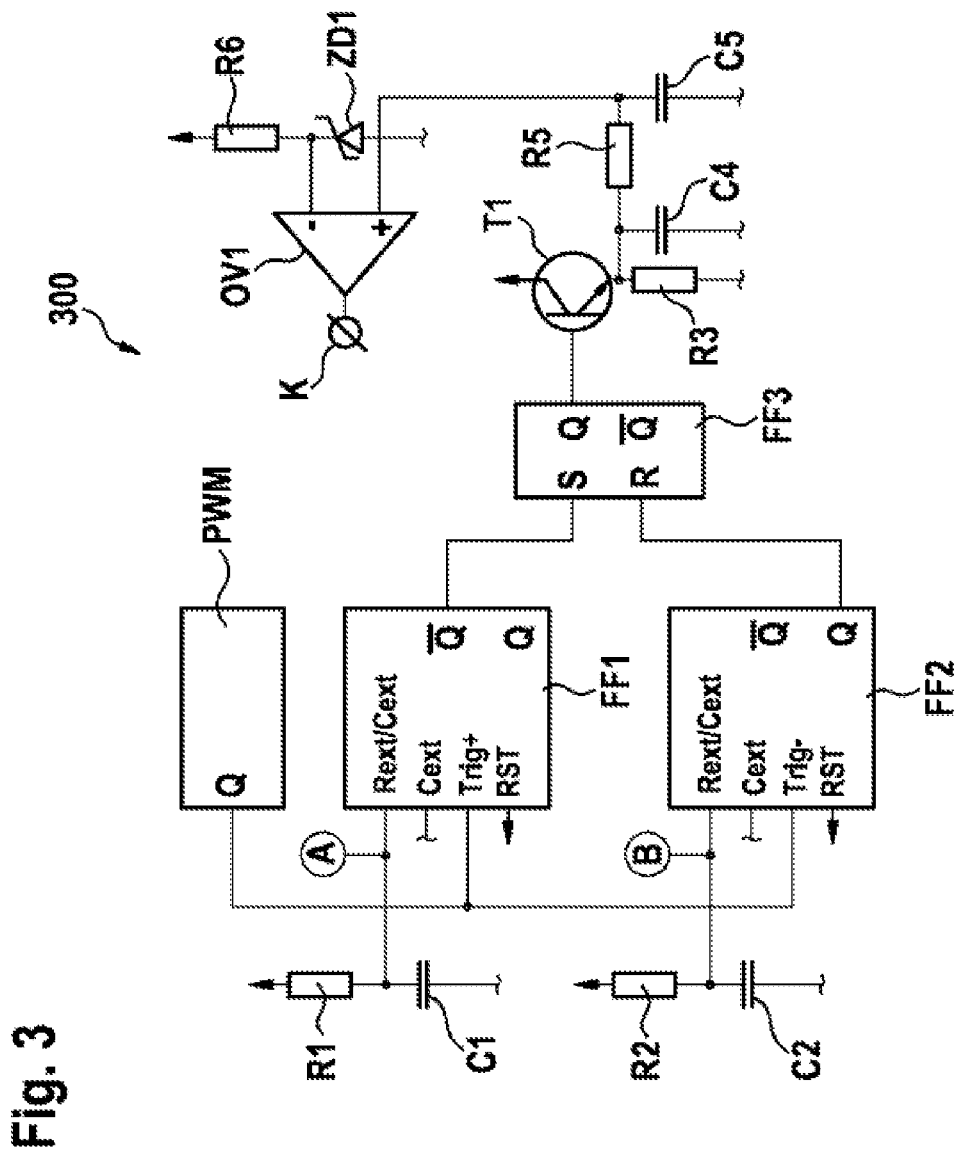
FIG. 3 shows a beam finder for actuating the electrode arrangement from FIG. 2.

FIG. 3 shows a beam finder 300 for actuating the electrode arrangement 200 from FIG. 2. A time element F1 is connected to the test point A, and a time element F2 to the test point B. When a measurement is carried out, the appropriate connection of the time element to the test point A or B respectively has a high impedance. Otherwise, the connection is connected to ground, thus implementing the functionality of the switch S1 or S2 respectively.

A clock generator PWM provides a rectangular signal, with which the ratio between a high output signal (High) and a low output signal (Low) can be influenced during each clock period. A rising edge of the rectangular signal provided by the clock generator PWM triggers the time element FF1, and a falling edge triggers the time element FF2. Unused connections of the time element FF1 and FF2 are connected to ground or to the supply voltage respectively.

A non-inverting output Q of the time element FF2 is connected to the R-input of an RS flip-flop FF3. In other embodiments, any other state memory can also be used, for example an appropriately connected T flip-flop. The inverting output $\overline{Q}$ of the time element FF1 is connected to the S-input of FF3. A non-inverting output Q of FF3 is connected to an integrator which comprises a transistor T1, a resistor R3 and a capacitor C4. The output of the integrator is connected to a low-pass filter, which is formed by a resistor R5 and a capacitor C5.

The output of the low-pass filter is connected to the non-inverting input of an operational amplifier OV1, to the inverting input of which is applied a constant voltage which is provided by a resistor R6 and a Zener diode ZD1. The operational amplifier OV acts as a comparator. If the voltage applied to the non-inverting input exceeds the voltage applied to the inverting input, then the output of the operational amplifier OV1 is set to a positive value (High). As an alternative to the simple comparator shown, a window comparator can also be used, the output of which outputs a signal which indicates whether or not the voltage provided by the low-pass filter lies between two predefined threshold values. The output of the operational amplifier OV1 is connected to a terminal K.

The components connected to the output Q of the RS flip-flop FF3 serve to provide a positive signal at the terminal K when a pulse which appears periodically at the output Q of FF3 exceeds a predefined length. This corresponds to a predefined difference between the capacitances C1 and C2 which is brought about by the dielectric object 120 in the region of the electrodes E0, E1 and E2. The signal at the terminal K corresponds to the determination of the dielectric object 120.

The flip-flops FF1 to FF3 serve to alternately determine the capacitances C1 and C2 and to compare them with one another. The chosen circuit arrangement enables the temporary storage of a value which refers to the capacitance of one of the capacitances C1, C2 while the other capacitance C2, C1 is determined to be avoided.

As an alternative to the diagram of FIG. 3, the capacitances C1 and C2 can also be determined and the pulses shown above evaluated in a number of other ways. For example, the pulses provided by the time elements FF1 and FF2 can first be integrated and only then compared with one another. Alternatively, one of the pulses can be inverted and shifted down by the voltage difference (High−Low) to then be fed to an integrator. Both the comparison and the evaluation can be carried out by a digital microcomputer, in which an analog-digital conversion and/or a digital-analog conversion can be carried out. The capacitances C1 and C2 can also be converted into digital values by means of a determination method different from by means of the time elements FF1 and FF2. In a further embodiment, each of the capacitances C1 and C2 can be determined by means of an oscillator and frequencies of the oscillators can be subtracted from one another.

The principle of operation of the interconnected flip-flops FF1 to FF3 of FIG. 3 is now explained in more detail with reference to FIG. 4.

Figure 4:
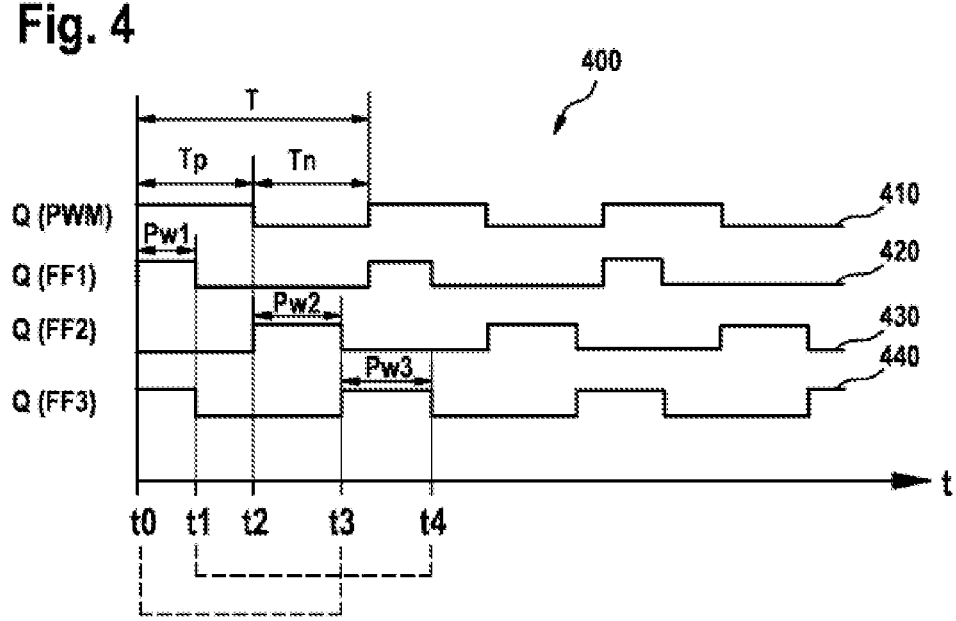
FIG. 4 shows a time diagram with characteristics at the beam finder from FIG. 3.

FIG. 4 shows a time diagram 400 with characteristics at the beam finder 300 from FIG. 3. A time is plotted in the horizontal direction. Four characteristics are plotted from top to bottom. The top characteristic 410 corresponds to the output Q of the clock generator PWM. The following characteristics 420 and 430 correspond to the outputs Q of the time elements FF1 and FF2 respectively. It must be noted that, although the output Q of the time element FF1 in FIG. 3 is not wired, the characteristic 420 refers to this output and not to the wired output $\overline{Q}$. The fourth characteristic 440 corresponds to the output Q of the RS flip-flop FF3.

Within a cycle T, the clock generator PWM generates the symmetrical rectangular signal shown in characteristic 410. A positive portion Tp and a negative portion Tn are of equal length. In other embodiments, an asymmetrical signal can also be generated by the characteristic 410 in which Tp and Tn are of unequal length. At time t0, the first time element FF1 is triggered by the rising edge of the first characteristic 410 in order to start a determination of the capacitance of C1. The output Q of the first time element FF1 is set to "High" and the capacitance C1 is charged via the resistor R1. At this time, the output Q of the second time element FF2 is "Low" which corresponds to a closed switch S2 in FIG. 2.

At time t1, the voltage at test point A has exceeded a predefined threshold value and the measurement is complete. The characteristic 420 switches back to "Low". The pulse duration Pw1 in the characteristic 420 between t0 and t1 depends on the determined capacitance of C1.

A corresponding determination of the capacitance C2 starts at time C2 with the falling edge of the characteristic 410. At time t3, the determination is complete and the pulse duration Pw2 of the characteristic 430 depends on the determined capacitance of C2.

In order to compare the pulse durations Pw1 and Pw2 with one another, the RS flip-flop FF3 is in each case set by the falling edge of the characteristic 430 and reset by the falling edge of the characteristic 420. Setting occurs at times t0 and t3; resetting at times t1 and t4 respectively. If the capacitances of C1 and C2 are equal, then the pulse lengths Pw1 and Pw2 are of the same length and the characteristic 440 is a symmetrical rectangular signal. In other words, in this case, Pw3 in characteristic 440 is the same length as Tp or Tn in characteristic 410.

By integrating the characteristic 440, a voltage which corresponds to the ratio between High and Low time of the characteristic 440 can be provided and, after passing through a low-pass filter, this voltage can be compared with a constant voltage. If the voltage provided by the low-pass differs from the constant voltage by more than a predefined amount, then the signal of the characteristic 440 has a mark-space ratio which implies the presence of a dielectric object 120 in the region of the electrodes E0 to E2 in FIG. 1.

Asymmetries, which may be caused by component spread or by parasitic effects between the components, can be compensated for in that the rectangular signal of the fourth characteristic 440 is made asymmetrical to a suitable extent. In this way, the beam finder 100 can be designed to be adjustable.

Figure 5:
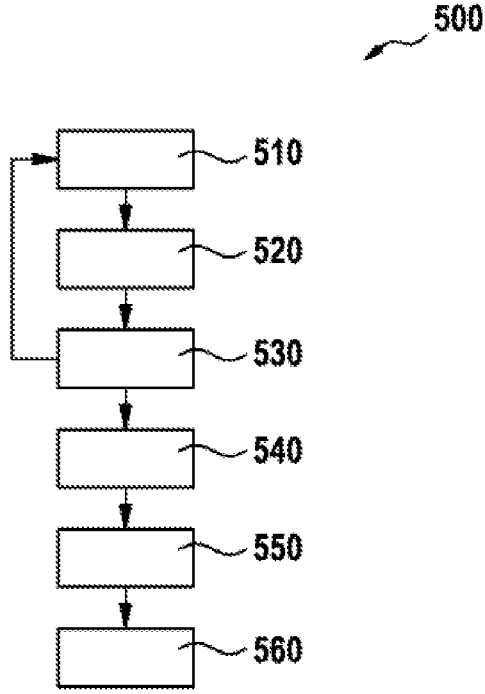
FIG. 5 shows a flow diagram of a method for beam finding.

FIG. 5 shows a method 500 for detecting a dielectric object 120. The method 500 comprises steps 510 to 560. In a first step 510, a clock signal is generated for controlling the capacitance measurements of C1 and C2. The first capacitance C1 is determined in step 520 and the second capacitance C2 in step 530. While the method 500 returns to the beginning and runs through once more, the difference between the two determined capacitances is determined in step 540. The determined difference is then compared with a threshold value in step 550. If the determined difference deviates from the threshold value by more than a predefined amount, then the presence of the dielectric object 120 in the region of the electrodes E0 to E2 is inferred. This result is output in step 560. It can be output, for example in a visual and/or audible manner, to a user of the beam finder 300.

The invention claimed is:

1. A device for detecting a dielectric object, comprising:
   a first electrode and a second electrode;
   a first device configured to determine a first capacitance which exists between the first electrode and a common reference point and which is influenced by the object;
   a second device configured to determine a second capacitance which exists between the second electrode and the common reference point and which is influenced by the object;
   a control unit configured to actuate the first and second devices, the control unit being configured to actuate the first and second devices in such a way that the determinations are carried out successively;
   an evaluation unit configured to detect the object when the determined capacitances differ from one another by more than a predefined amount; and
   a switching device configured to electrically connect the electrode of the device which is not actuated at any one time to the common reference point.

2. The device as claimed in claim 1, further comprising a third electrode arranged in the region of the first electrode and the second electrode.

3. The device as claimed in claim 2, wherein the third electrode is arranged on a respective side of the first electrode and the second electrode which faces away from the dielectric object.

4. The device as claimed in claim 1, wherein the first and second devices are configured to output time signals, the lengths of which in each case depend on the determined capacitances, and wherein the evaluation unit is configured to provide a time signal, the length of which depends on the difference between the capacitances.

5. The device as claimed in claim 1, wherein the control unit is configured to periodically actuate the first and second devices with the same frequency, and wherein a phase relationship between the periodic actuations is varied to compensate for different capacitances in the absence of the object.

6. The device as claimed in claim 1, further comprising a multiplicity of devices configured to determine capacitances between an electrode and the common reference point, wherein the control unit is configured to actuate only one of the devices at each point in time and the switching device is configured to electrically connect the electrodes of all devices which are not actuated to the common reference point.

7. A method for detecting a dielectric object, comprising:
   determining a first capacitance which exists between a first electrode and a common reference point and which is influenced by the object;
   determining a second capacitance which exists between a second electrode and the common reference point and which is influenced by the object, the first and second capacitances being determined successively;
   detecting the object when the determined capacitances differ from one another by more than a predefined amount; and
   during the capacitance determination via one of the electrodes, electrically connecting the respective other electrode to the common reference point.

\* \* \* \* \*